(12) United States Patent
Shinomura et al.

(10) Patent No.: US 7,474,778 B2
(45) Date of Patent: Jan. 6, 2009

(54) ULTRASONOGRAPH

(75) Inventors: Ryuichi Shinomura, Saitama (JP); Hiroshi Kanda, Saitama (JP); Satoshi Tamano, Chiba (JP)

(73) Assignee: Hitachi Medical Corporation, Tokyo (JP)

( * ) Notice: Subject to any disclaimer, the term of this patent is extended or adjusted under 35 U.S.C. 154(b) by 814 days.

(21) Appl. No.: 10/507,327

(22) PCT Filed: Mar. 11, 2003

(86) PCT No.: PCT/JP03/02858

§ 371 (c)(1), (2), (4) Date: Sep. 10, 2004

(87) PCT Pub. No.: WO03/075768

PCT Pub. Date: Sep. 18, 2003

(65) Prior Publication Data

US 2005/0124880 A1 Jun. 9, 2005

(30) Foreign Application Priority Data

Mar. 12, 2002 (JP) ............................. 2002-066591

(51) Int. Cl.
*G06K 9/00* (2006.01)
(52) U.S. Cl. ..................... 382/131; 128/922; 367/153; 378/21
(58) Field of Classification Search ................. 382/100, 382/128, 129, 130, 131, 132, 133; 128/922; 367/38, 50, 87, 117, 140, 153, 154; 378/4–27
See application file for complete search history.

(56) References Cited

U.S. PATENT DOCUMENTS

| | | | | | |
|---|---|---|---|---|---|
| 3,979,711 | A | * | 9/1976 | Maginness et al. | 367/87 |
| 4,119,938 | A | * | 10/1978 | Alais | 367/87 |
| 4,159,462 | A | * | 6/1979 | Rocha et al. | 367/97 |
| 4,532,615 | A | * | 7/1985 | Ballinger | 367/87 |
| 5,381,385 | A | * | 1/1995 | Greenstein | 367/140 |
| 5,548,561 | A | * | 8/1996 | Hussain et al. | 367/7 |
| 5,922,962 | A | * | 7/1999 | Ishrak et al. | 73/632 |
| 6,130,641 | A | * | 10/2000 | Kraeutner et al. | 342/179 |

FOREIGN PATENT DOCUMENTS

JP 02-017297 1/1990

(Continued)

*Primary Examiner*—Anand Bhatnagar
(74) *Attorney, Agent, or Firm*—Antonelli, Terry, Stout & Kraus, LLP.

(57) ABSTRACT

An ultrasonic diagnostic apparatus includes an ultrasound probe having two-dimensionally arranged transducer elements for transmitting and receiving ultrasonic waves to an object, a transducer element selector for selecting transducer elements used in transmission and reception, a signal processing unit for applying a delay to a signal received by a selected transducer element, an image processing unit for generating an image based on the output signal of the signal processing unit, and an image display unit. The image processing unit stores a first ultrasound image obtained by a scan of a first transducer arrangement selected by the transducer element selector and a second ultrasound image obtained by a scan of a second transducer arrangement selected by the transducer element selector so as to irradiate an ultrasound beam in a different direction than the beam direction of the first transducer arrangement, and combines the first ultrasound image and the second ultrasound image.

19 Claims, 6 Drawing Sheets

FOREIGN PATENT DOCUMENTS

| | | |
|---|---|---|
| JP | 02-017298 | 1/1990 |
| JP | 07-178086 | 7/1995 |
| JP | 2000-325344 | 11/2000 |
| JP | 2001-157677 | 6/2001 |
| JP | 2001-286467 | 10/2001 |

* cited by examiner

Fig. 7

ULTRASONOGRAPH

TECHNICAL FIELD

The present invention relates to an ultrasonic diagnostic apparatus, and, more particularly, to an effective technique for using, in a three-dimensional scan of an object, a two-dimensional array probe in which a plurality of transducer elements for transmitting and receiving an ultrasonic wave are two-dimensionally arranged.

BACKGROUND OF THE INVENTION

Along with recent developments in the performance of ultrasonic diagnostic apparatuses and in the use of a ultrasound diagnostic techniques, ultrasonic diagnostic apparatuses are being utilized in various fields of diagnosis, and a three-dimensional display of an image is now desired in performing a diagnosis using ultrasound. Usually, it was necessary for displaying a three-dimensional image display to collect a plurality of tomographic images of an object to be examined at a plurality of predetermined distances and to reconstruct a three-dimensional image by joining the outlines of an organ or the like which forms an imaging object (observing object) extracted from those tomographic images.

However, when an ultrasonic diagnostic apparatus has a two-dimensional probe, including two-dimensionally arranged transducer elements in a flat surface, and an aperture is formed by concentric multiple rings on the two-dimensional ultrasound probe, the direction of forming an ultrasound beam is limited to the direction of a normal line the probe surface. Accordingly, a three-dimensional image could not be generated by utilizing the above-described combination of ultrasound beams.

Further, because an ultrasonic diagnostic apparatus employing a sparse array technique performs a sector scan with an ultrasound beam without moving the aperture, it is impossible to cross ultrasound beams in the ultrasound measurement. Accordingly, it was impossible to apply a method of generating a tomographic image using a combination of ultrasound beams.

Japanese Unexamined Patent Publication No. Hei. 9-234199 discloses an ultrasonic diagnostic apparatus including an ultrasound probe having a plurality of transducers arranged in a scan direction and a lens direction for transmitting and receiving an ultrasonic wave, which apparatus further includes selecting means for selecting a transducer to be driven from among the plurality of transducers, ultrasound transmitting means for driving the transducer selected by the selecting means in the scan direction and in the lens direction on the basis of predetermined delay data so as to generate a transmitted beam having a focal point at a certain depth in the scan direction and the lens direction, inputting means for inputting information on an object to be examined, and control means for controlling the ultrasound transmitting means in accordance with the information on the object. However, a compound scan using a two-dimensional array probe is not disclosed.

An object of the present invention is to provide a technique with which a tomographic image of high resolution can be collected by means of compound scan while the transducers of a two-dimensional ultrasound transducer array are switched, and to provide a technique with which the image quality can be improved by using a two-dimensional ultrasound transducer array without increasing the scale of the apparatus.

SUMMARY OF THE INVENTION

To solve the above-described problem, the object of the present invention is to provide a technique with which a tomographic image can be collected using a two-dimensional array ultrasound probe. Another object of the present invention is to provide a technique with which the image quality of a diagnostic image can be improved using a two-dimensional array ultrasound probe without increasing the apparatus scale.

BRIEF DESCRIPTION OF THE DRAWINGS

FIGS. 2(*a*) and 2(*b*) are diagrams illustrating the structure of an ultrasonic diagnostic apparatus according to Embodiment 1 of the present invention.

FIGS. 3(*a*) and 3(*b*) are diagrams illustrating the positional relation between an ultrasonic wave received by each transducer element according to Embodiment 1 and a focal point F.

FIGS. 5(*a*), 5(*b*) and 5(*c*) are diagrams illustrating the structure of an ultrasonic diagnostic apparatus according to Embodiment 2 of the present invention.

BEST MODE FOR CARRYING OUT THE INVENTION

Hereinafter, various embodiments of the present invention will be described with reference to the drawings. In the drawings, constituents having an identical function are given an identical reference numeral designation, and a repeated explanation thereof is omitted.

EMBODIMENT 1

Figure 1:
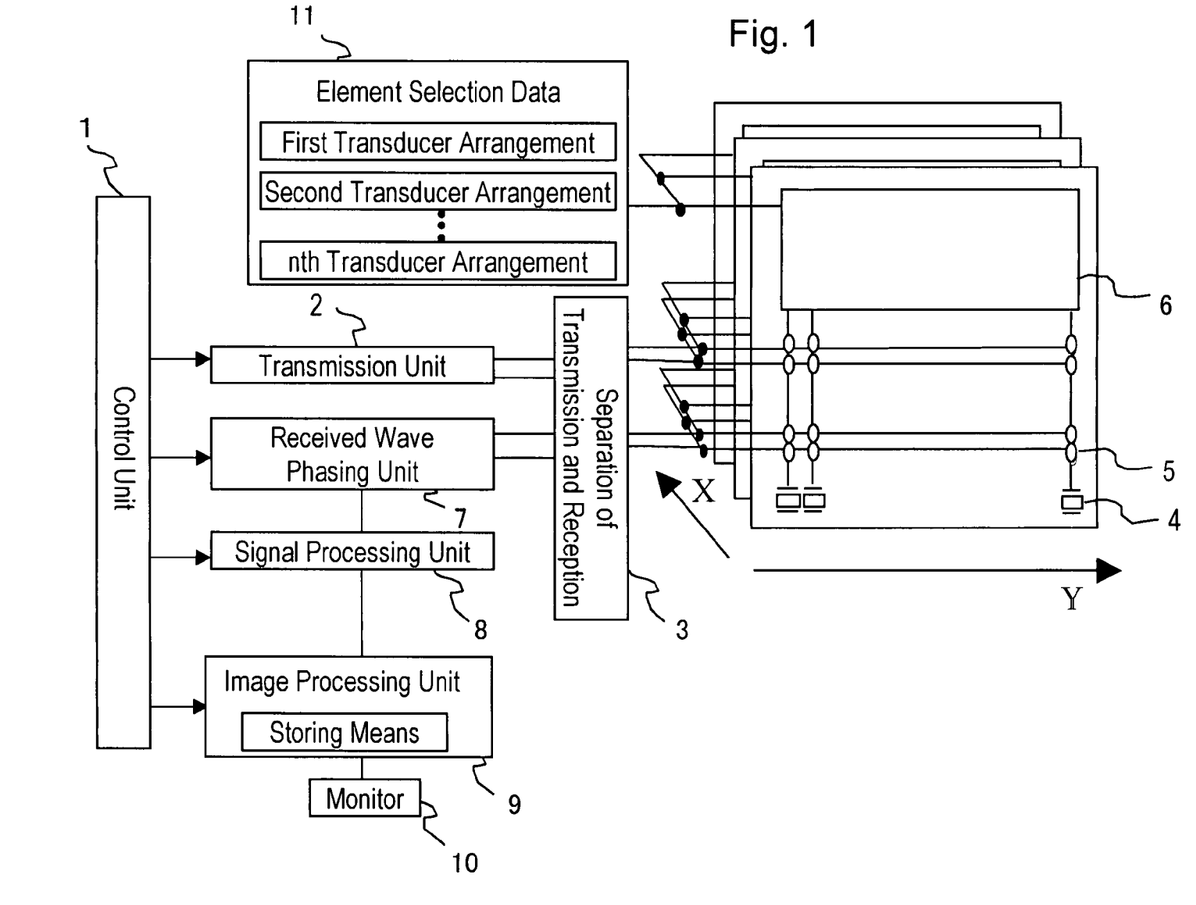
FIG. 1 is a diagram illustrating the structure of an ultrasonic diagnostic apparatus according to Embodiment 1 of the present invention.

FIG. 1 shows the structure of an embodiment of an ultrasonic diagnostic apparatus according to the present invention. This ultrasonic diagnostic apparatus is designed to form an ultrasound beam with a two-dimensional transducer array and for scanning the beam to obtain an ultrasound image of a portion under diagnosis inside an object to be examined in real time. The apparatus includes ultrasound transducer 4, element selection data unit 11, transmission unit 2, received wave phasing unit 7, transmission-reception separating circuit 3, signal processing unit 8, image processing unit 9, monitor 10, and control unit 1.

A probe is designed to transmit and receive an ultrasonic wave inside the object, and for this purpose it has a plurality of two-dimensionally arranged transducers 4, 4, . . . Those transducers 4, 4, . . . are two-dimensionally arranged, with 1 to m elements being arranged in the X direction and 1 to n elements being arranged in the Y direction in a plane.

Transducers 4, 4, . . . are connected with a connection switch group 5 combined with an arbitrary channel of the phasing circuit. This connection switch group 5 is connected to switch control unit 6 for controlling its switching operation.

Element selection data unit 11 is designed to store element selection data based on the transducer array, as well as ultrasound scan information for forming an aperture for ultrasound transmission and reception. The data read out therefrom is transmitted to switch control unit 6, and on/off switching of connection switch group 5 is determined by control provided by the switch control unit 6 so as to form an aperture for ultrasound transmission and reception.

Transmission unit 2 is designed to apply a transmission signal having a delay to transducers 4 of the probe forming the aperture of the ultrasound transmission and reception so that the ultrasonic waves are focused on a desired focal point. Received wave phasing unit 7 is designed to perform a desired focus processing and phase addition on a reflected echo signal received by transducer 4 and to form a received beam. Transmission-reception separating circuit 3 is designed to switch connection of a transducer 4 to the transmission unit 2 during transmission and to the received wave phasing unit 7 during reception.

Signal processing unit 8 is designed to receive the received signal sent from received wave phasing unit 7, to perform processings including detection, compression, and edge enhancement, and to obtain data for one scan line. Image processing unit 9 is designed to receive the data sent from signal processing unit 8 and perform scan conversion, interpolation and the like, so as to present an image on monitor 10. Monitor 10 is designed to display the data input from image processing unit 9 as an ultrasound image. Control unit 1 is designed to control the operations of the above-described components.

Figure 2:
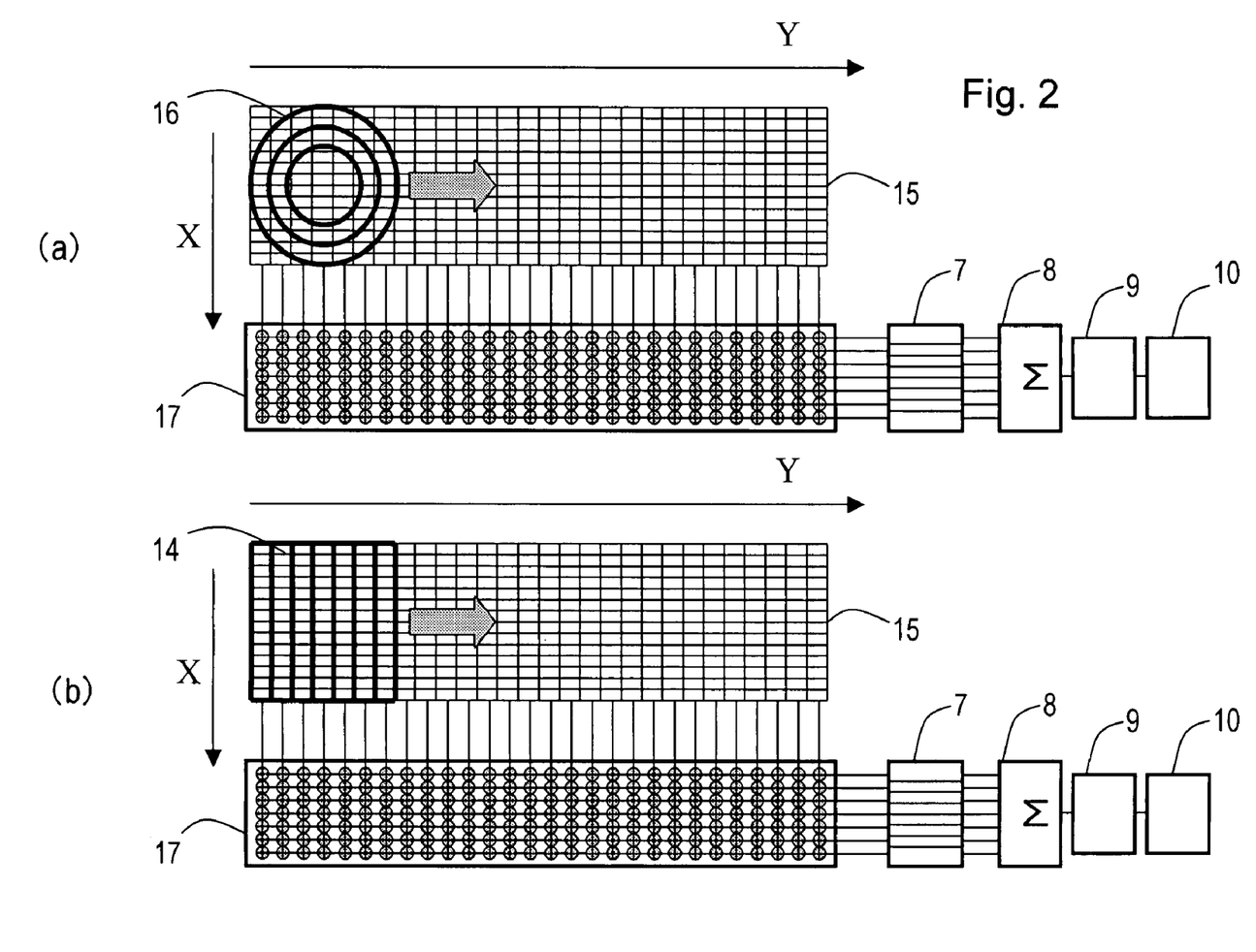

FIGS. 2(*a*) and 2(*b*) are diagrams illustrating the structure of the ultrasonic diagnostic apparatus according to Embodiment 1 of the present invention. Specifically, FIG. 2(*a*) is a diagram illustrating the structure in the case where the aperture is formed by concentric multiple rings to collect a tomographic image, and FIG. 2(*b*) is a diagram illustrating the structure in the case where the transducer elements are bundled into strip shapes to collect a tomographic image. In these figures, numerical reference 7 represents a phasing circuit, numerical reference 8 represents an adder, numerical reference 9 represents an image processing unit, numerical reference 10 represents a monitor, numerical reference 15 represents a transducer element, numerical reference 16 represents an aperture formed by bundled rings, numerical reference 17 represents a switch array, and numerical reference 14 represents an aperture formed by bundled strip-shaped pieces. Hereinafter, a one-dimensional scan in the Y direction performed by the ultrasonic diagnostic apparatus according to Embodiment 1 will be described.

As shown in FIGS. 2(*a*) and 2(*b*), the ultrasonic diagnostic apparatus according to Embodiment 1 includes an ultrasound probe in which transducer elements 15 are two-dimensionally arranged, a switch array 17 is disposed in the side of an ultrasound probe for selecting a transducer element to be used in ultrasound transmission and reception, a received wave phasing unit 7 is provided for applying a delay for received wave phasing to a received signal from the ultrasound probe, an image processing unit 9 is provided for generating a tomographic image from information on an intersecting point of an ultrasound beam obtained by the multiple ring transducer and that obtained by the strip-shaped transducer, and a monitor 10 is used for displaying the tomographic image that is generated. Although switch array 17 is installed in the ultrasound probe according to Embodiment 1, of course, it may be provided in the main body of the apparatus. However, installing switch array 17 in the ultrasound probe leads to a reduction in the number of signal lines connecting the ultrasound probe and the main body. In FIGS. 2(*a*) and 2(*b*), the structure of the transmission system is omitted.

The ultrasonic diagnostic apparatus according to Embodiment 1 includes control means for controlling the switch array 17 to select transducers arranged in ring shapes from among the two-dimensionally arranged transducer elements 4 so as to form ring-like apertures for transmitting and receiving an ultrasonic wave and to scan the ultrasonic wave in a Y-axis direction designated by the arrow with an aperture 16 formed by bundled rings. The control means also operates to control the switch array 17 to select transducers arranged in strip shapes from among the two-dimensionally arranged transducer elements 4 so as to form apertures for forming an ultrasound beam in an oblique direction different from a normal line direction of the probe surface. Meanwhile, the control means controls the received wave phasing unit 7 in correspondence with the shape of the aperture and the beam direction in the case of forming any aperture.

In FIGS. 2(*a*) and 2(*b*), the ultrasound probe according to Embodiment 1 includes a plurality of two-dimensionally arranged transducer elements for transmitting and receiving ultrasonic waves to/from the inside of the object to be examined (not shown), so as to collect an ultrasound signal. Those transducer elements 4 are arranged in a plane in a longitudinal axis direction representing one direction of the two-dimensional array of transducer elements 4 (Y-axis direction in FIG. 2(*a*)) and in a minor axis direction representing another direction (X-axis direction in FIG. 2(*a*)) perpendicular to the longitudinal axis direction.

In the arrangement of transducer elements 4, for example, twenty-eight transducer elements 4 are arranged in the Y-axis direction, and the surface of ultrasound transmission and reception of transducer elements 4 is a plane oriented with respect to the transmitting direction of the ultrasound waves. However, the arrangement of transducer elements 4 in the Y-axis direction is not limited to a plane surface, and it also may be determined so that the surface of the array of transducer elements 4 forms an arc that is convex in shape with respect to the transmitting direction of the ultrasound waves.

Further, in the minor axis direction (X-axis direction in FIG. 2(*a*)) fourteen transducer elements 4 are arranged, and the surface of ultrasound transmission and reception of the transducer elements 4 is a plane oriented with respect to the transmitting direction of the ultrasound waves. Meanwhile, in a similar manner, as to the transducer elements in the Y direction, transducer elements 4 may be arranged in the X-axis direction so as to form an arc that is convex in shape in the transmitting direction of the ultrasound waves.

Switch array 17 includes element selecting switches, the number of which is equal to the number of channels of the received wave phasing unit $7 \times$ the number of transducer elements in the Y-axis direction (direction of ultrasound scanning) × the number of transducer elements in the X-axis direction, i.e. $8 \times 28 \times 14 = 3136$. Particularly, as shown in FIGS. 2(*a*) and 2(*b*), $8 \times 28 = 244$ element selecting switches, according to Embodiment 1, are arranged in a matrix shape at each row in the X-axis direction, and an arbitrary channel of the received wave phasing unit 7 can be connected to any row of transducer elements 4 by respectively switching the element selecting switches. Accordingly, by shifting the element selecting switches forming the switch array 17, a multiple ring aperture 16, e.g. formed by Fresnel rings, and a strip-shaped aperture 14 are sequentially moved in the X and Y directions shown by arrows on a probe surface so as to transmit and receive an ultrasound beam and acquire three-dimensional data. However, an actual ultrasonic diagnostic apparatus requires several dozens to several hundreds of transducer elements for forming apertures.

Received wave phasing unit 7 includes a plurality of phasing circuits corresponding to the larger number between the arranged element number of concentric rings and that of the rectangular element arrays, e.g. eight-channel phasing circuits. Meanwhile, the structure of the phasing circuit may be similar to a conventional one. Further, according to Embodiment 1, ultrasound beams are sequentially formed by Fresnel-ring aperture 16 and strip-shaped aperture 14. Therefore, the phasing circuit group reads out and sets phasing data corresponding to the aperture from a table (not shown) in response to an aperture instruction signal received from the control unit (not shown).

Signal processing unit 8 may be provided in the form of a known adder for summing up the received signals output from the received wave phasing means having eight channels forming received wave phasing unit 7 after phasing, thus forming an ultrasound beam.

Signal processing unit 9 includes storing means for temporarily storing a first ultrasound image generated by an ultrasound beam obtained by transmitting and receiving an ultrasonic wave with Fresnel-ring aperture 16 and corresponding to the direction of a normal line of the probe surface and a second ultrasound image generated by an ultrasound beam obtained by transmitting and receiving an ultrasonic wave from strip-shaped aperture 14 and being oblique with respect to the normal line direction of the probe. Further, image processing unit 9 includes image calculating means (not shown) for generating one tomographic image and/or three-dimensional image using a known imaging method referred to as a compound scan, in which a tomographic image is generated on the basis of an ultrasound tomographic image obtained by scanning ultrasound beams in various beam directions from tomographic information on a position where ultrasound beams intersect, i.e., using information of a phased received signal from a position where ultrasound beams intersect. Further, image processing unit 9 has converting means for performing known volume rendering processing, surface rendering processing, and the like for converting the obtained three-dimensional image into a two-dimensional image to be displayed (three-dimensional ultrasound image). The details of such a compound scan are mentioned in Robert R. Entrekin, "Real-Time spatial compound imaging-Technical performance in vascular applications", Acoustical Imaging, Vol. 25, 2000.

Next, operations for collecting an ultrasound tomographic image using Fresnel-ring aperture 16 and strip-shaped aperture 14 according to Embodiment 1 will be described with reference to FIGS. 2(*a*) and 2(*b*). In the following description, Fresnel-ring aperture 16 is formed by bundling transducer elements 4 in three ring-shapes, and strip-shaped aperture 14 is formed by bundling eight strip lines of transducer elements 4 in the X-axis direction. However, the number of rings and strip lines is not limited thereto.

As shown in FIG. 2(*a*), the control means operates to the switch array 17 on and off to bundle two-dimensionally arranged transducer elements 4 into three ring shapes, and thus, a Fresnel-ring aperture 16 is formed. At this time, the control means sets phasing data at each channel of the received wave phasing unit 7 so as to form a focal point in a direction of a normal line extending from central points of those three rings. That is, transducer elements 4 are selected so that the distance between each of the transducer elements 4 forming an identical ring and the focal point becomes substantially the same, and predetermined phasing data is supplied to the phasing circuit connected with the selected transducer element group.

Figure 3:
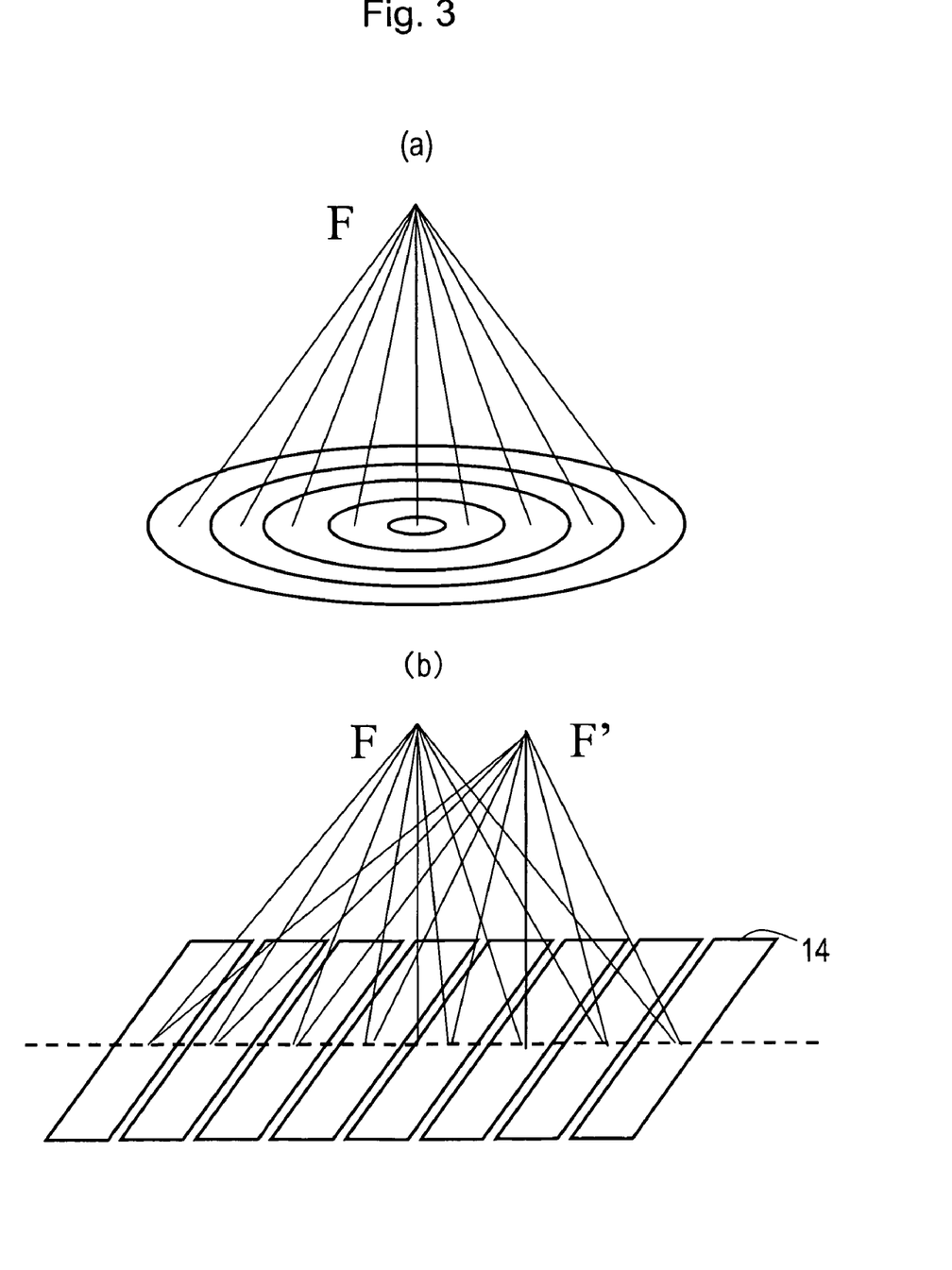

Here, a signal is output from the adder unit by transmitting and receiving an ultrasonic wave with aperture 16 and which has been made into an ultrasound beam extending equally in any direction, i.e. extending in a normal line direction from the central point of aperture 16. The positional relation between an ultrasonic wave received by each transducer element 4 and the focal point F is shown in FIGS. 3(*a*) and 3(*b*). As is clear from FIGS. 3(*a*) and 3(*b*), the focal point formed by aperture 16 is in the direction of a normal line of the Fresnel rings.

Next, aperture 16 is moved in the direction of the arrow shown in FIG. 2(*a*) while the control means controls switching of the respective element selecting switches of the switch array 17 at every ultrasound transmission and reception to retain Fresnel-ring aperture 16; and, thus, a linear scan can be performed in a state where the ultrasound beam direction is retained in the normal line direction.

When a scan using Fresnel-ring aperture 16 is completed, the control means then switches the switch array 17 on and off so that strip-shaped aperture 14 is formed by a plurality of transducer element arrays in the Y-axis direction, as shown in FIG. 2(*b*). At this time, the control means controls the received wave phasing unit 7 to adjust the phasing data supplied to a signal received at each transducer element array so that an ultrasound beam from aperture 14, formed by eight transducer element arrays, is directed in an oblique direction which does not coincide with the normal line direction at the central point of aperture 14.

Here, a signal output from the adder, by transmitting and receiving an ultrasonic wave with aperture 14, is made into an ultrasound beam having a predetermined angle with respect to the ultrasound beam of aperture 16. That is, when the central points of aperture 16 and of aperture 14 are identical, focal points F and F' are respectively located at different positions, as shown in FIG. 3(*b*). However, in contrast to the ultrasound beam of Fresnel-ring aperture 16, the oblique angle $\theta$ of the ultrasound beam of the strip-shaped aperture 14 can be arbitrarily set with respect to the surface of the transducer element array of aperture 14 by adjusting the phasing data of each row of transducer elements.

At this time, aperture 14 is moved in the direction of the arrow shown in FIG. 2(*b*) while the control means switches each transducer selecting switch of switch array 17 on and off in synchronism with the cycle of ultrasound transmission and reception to retain strip-shaped aperture 14, and a linear scan, i.e. an oblique scan, can be performed in a state where the ultrasound beam direction is retained in an oblique direction. According to Embodiment 1, the ultrasound scan with strip-shaped aperture 14, as will be described below, is performed in two different directions. Therefore, when the scan with focal point F' shown in FIG. 3 is completed, the control means then conducts a scan at another oblique angle (e.g. $(-\theta)$ shown in FIG. 4). Meanwhile, this scan at another oblique angle is not essential, and the oblique scan may be performed at only one oblique angle. However, by scanning at two or more oblique angles, the image quality of the tomographic image obtained can be improved.

Figure 4:
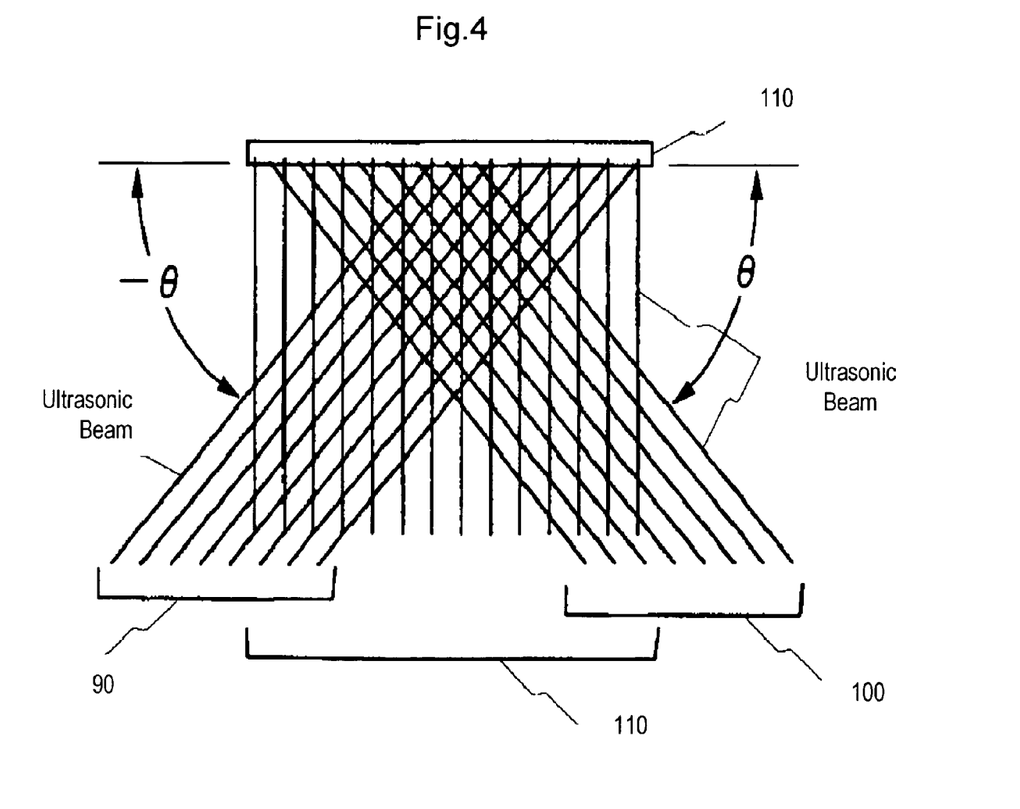
FIG. 4 is a diagram illustrating an ultrasound tomographic image obtained with the scan of an ultrasound beam in a different beam direction than that according to Embodiment 1.

When tomographic data on an identical portion are obtained with ultrasound scans using Fresnel-ring aperture 16 and strip-shaped aperture 14, the control means operates to calculate one ultrasound tomographic image from tomographic information on an intersecting point of ultrasound beams of an ultrasound tomographic image which image processing unit 9 obtains by ultrasound beam scanning in different beam directions, as shown in FIG. 4. Next, image processing unit 9 outputs the ultrasound tomographic image to the monitor 10, and presents it on the display surface of the monitor 10.

Thus, in the ultrasonic diagnostic apparatus according to Embodiment 1, an ultrasound beam scan in the normal line direction of the probe surface is performed with Fresnel-ring aperture 16, an ultrasound beam scan in the oblique direction, which is different from the normal line direction of the probe surface, is performed with strip-shaped aperture 14, and ultrasound data acquired with the respective apertures is calculated and formed into an ultrasonic image. Accordingly, the image quality of the ultrasonic diagnostic apparatus can be improved without increasing the apparatus scale, i.e. with a fewer number of channels of the received wave phasing unit 7 than that of the transducer elements 4.

Meanwhile, in the ultrasonic diagnostic apparatus according to Embodiment 1, Fresnel ring aperture 16 and strip-shaped aperture 14 are respectively formed in an area surrounded by the same number of transducer elements respectively in the X-axis and Y-axis directions, e.g. fourteen transducer elements in the X-axis direction and eight in the Y-direction. However, as mentioned above, the actual apparatus structure is not limited thereto, and aperture 16 and aperture 14, of course, may be formed respectively in areas including another number of transducer elements. Further, aperture 16 and aperture 14, of course, may be formed in an area including another number of transducer elements 4.

In the ultrasonic diagnostic apparatus according to Embodiment 1, ultrasound scans of aperture 16 and of aperture 14 are sequentially performed and a tomographic image of high image quality is generated from tomographic images collected in these scans. However, for instance, the following may also be applicable: the main body or the probe of the ultrasonic diagnostic apparatus according to Embodiment 1 may be provided with a mode of displaying a tomographic image obtained with an ultrasound scan consisting of either aperture 16 or aperture 14 and a mode of displaying a tomographic image combining tomographic images obtained with an ultrasound scan of aperture 16 and aperture 14 using a compound scan image forming method. With this structure, a region of interest (ROI) is detected on the basis of a tomographic image obtained in the ultrasound scan mode of either aperture 16 or aperture 14; the ROI requiring its tomographic image of high image quality is ultrasound scanned by aperture 16 and aperture 14, and the mode is switched so as to generate a tomographic image by combining the obtained tomographic images to be presented. By thus switching into the mode of generating and presenting a tomographic image combining the obtained tomographic images, ultrasound measurement can be performed in both ways suitable for detecting an ROI which requires real-time processing (display), rather than image quality, and for image display for definite diagnosis, which requires high image quality, whereby both diagnostic efficiency and diagnosability can be improved.

Meanwhile, according to Embodiment 1, all signals of one transducer array of the strip-shaped transducers are given the identical phasing data. However, with this structure, focusing in the row direction is not performed, and so the image quality might be unfavorable. Accordingly, when the row is long, a phasing circuit may be installed which divides fourteen transducers into e.g. five groups respectively consisting of two, three, four, three, and two transducers and which performs focusing in the row direction on the respective transducer groups.

EMBODIMENT 2

Figure 5:
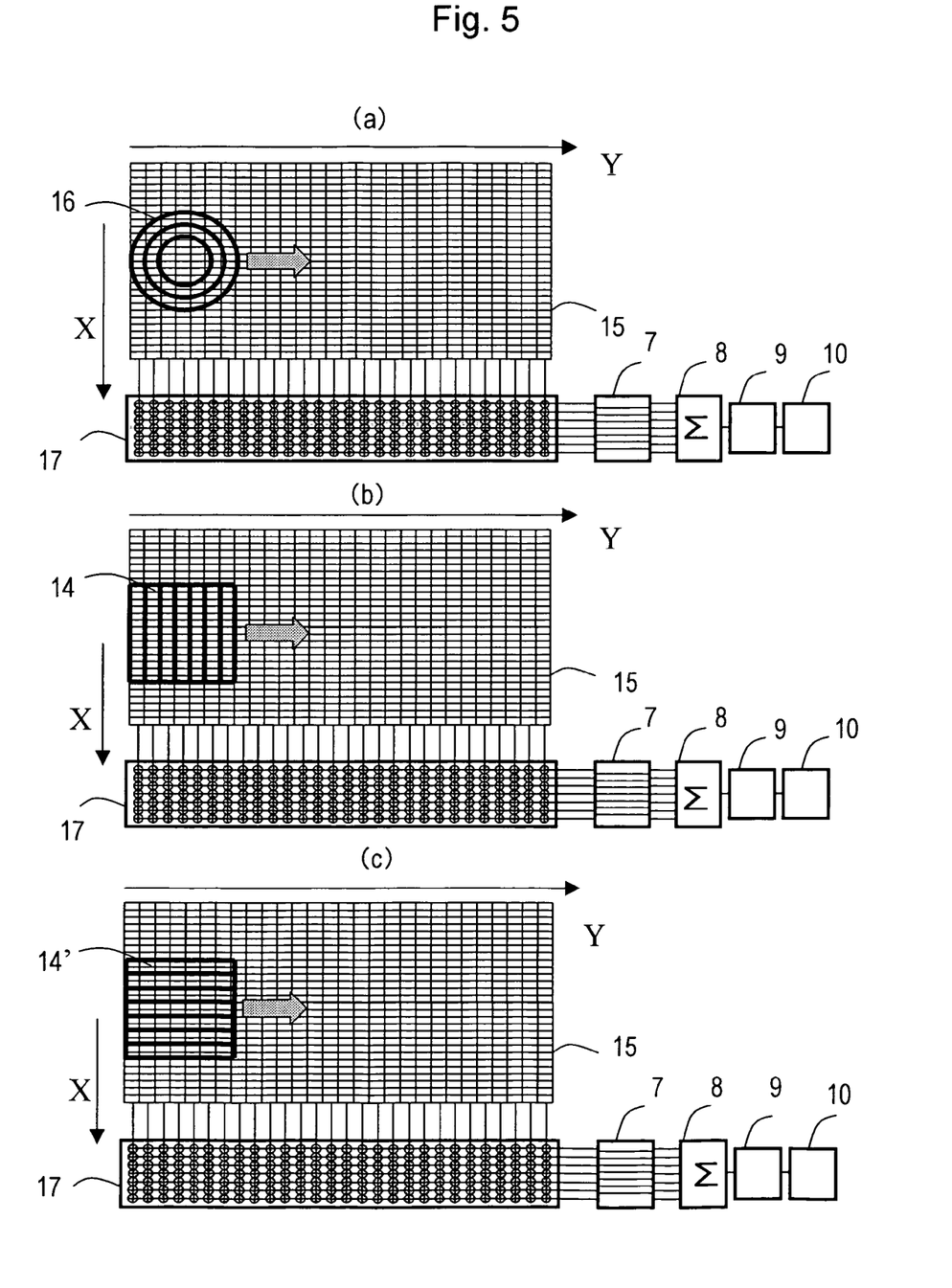

FIGS. 5(a), 5(b) and 5(c) are diagrams illustrating the structure of an ultrasonic diagnostic apparatus according to an Embodiment 2 of the present invention. Specifically, FIG. 5(a) is a diagram illustrating the structure where a tomographic image is collected by an aperture formed by concentric multiple rings, and FIG. 5(b) is a diagram illustrating the structure where a tomographic image is collected by transducer elements which are bundled into strip shapes. Meanwhile, in the ultrasonic diagnostic apparatus according to Embodiment 2, a larger number of transducer elements 4 is provided than in the two-dimensional array probe according to Embodiment 1, scans of aperture 16 and aperture 14 are performed in both the Y-axis and X-axis directions, and a plurality of ultrasonic tomographic images thus obtained are formed into a three-dimensional ultrasound image. Other structural features are similar to Embodiment 1. Accordingly, in the following description, the three-dimensional ultrasound image obtained by two-dimensional scans of apertures 16 and 14 along the probe surface will be described in detail.

As shown in FIGS. 5(a) and 5(b), the two-dimensional array probe according to Embodiment 2 includes a larger number of transducer elements in the X-axis direction than that provided in the two-dimensional array probe according to Embodiment 1. That is, the two-dimensional array probe according to Embodiment 2 includes 27×28=756 transducer elements 4. Meanwhile, in the same manner as in Embodiment 1, Fresnel-ring aperture 16 and strip-shaped aperture 14, respectively, form areas surrounded by 14×8=112 transducer elements 4.

In the ultrasonic diagnostic apparatus according to Embodiment 2, as shown in FIG. 5(a), aperture 16 is formed in an area on the probe surface when Fresnel-ring aperture 16 is formed in the area of 14×8 transducer elements. Accordingly, aperture 16 can perform a scan in both the arrow direction (Y-axis direction) and the X-axis direction shown in FIG. 5(a). Here, aperture 16 is moved in the Y-axis direction to collect a tomographic image while its position in the X-axis direction is fixed, and then it is moved in the X-axis direction for a predetermined number of transducer elements. After that, it is moved in the Y-axis direction again without scanning in the X-axis direction. In this manner, a tomographic image is obtained. Those operations (scanning) are repeated while aperture 16 moves from one end to the other end in the X-axis direction, whereby a plurality of tomographic images in the Y-axis direction can be collected without moving the two-dimensional array probe, the moving distance in the X-axis direction of which is the length of transducer elements 4 in the X-axis direction. However, because an ultrasound beam formed by Fresnel-ring aperture 16 runs in a normal-line direction of the probe surface, a tomographic image obtained by the scan of aperture 16 is collected by an ultrasound beam perpendicular to the probe surface as in Embodiment 1, as described above. Further, aperture 16 performs scans in the X-axis and Y-axis directions, while the control means controls switching of each transducer selecting switch forming switch array 17 in synchronism with the cycle of ultrasound transmission and reception to retain aperture 16.

On the other hand, as shown in FIG. 5(b), strip-shaped aperture 14, formed by 14×8 transducer elements, is also formed in an area of the probe surface. Accordingly, in a similar manner to aperture 16, aperture 14 can perform a scan in both the arrow direction (Y-axis direction) shown in FIG. 5(b) and the X-axis direction. Here, while the position of aperture 14 in the X-axis direction is fixed, aperture 14 is moved in the Y-axis direction to collect a tomographic image, and then it is moved in the X-axis direction for a predetermined number of transducer elements. After that, aperture 14 is moved in the Y-axis direction again without moving in the X-axis direction. In this manner, a tomographic image is obtained. Those operations are repeated while aperture 14 is moved from one end to the other end in the X-axis direction, whereby a plurality of tomographic images in the Y-axis direction can be obtained without moving the two-dimensional array transducer, that moving distance in the X-axis direction of which is the length of transducer elements 4 in the X-axis direction.

Meanwhile, as in Embodiment 1 described above, the ultrasound beam of aperture 14 according to Embodiment 2 runs in a direction other than the normal-line direction of the probe surface. Further, the ultrasound beam direction of aperture 14 is inclined in a direction corresponding to the scan direction of aperture 14, i.e. the Y-axis direction. By thus inclining the ultrasound beam of aperture 14, an ultrasound image on the same cross section as that collected by aperture 16 is collected with the oblique ultrasound beam. Further, aperture 14 performs scans in the X-axis and Y-axis directions while the control means controls switching of each transducer selecting switch forming switch array 17 in synchronism with the cycle of ultrasound transmission and reception to retain aperture 14. Further, a tomographic image of the same cross section may be collected by again changing the oblique angle and the inclining direction of the ultrasound beam.

Next, in the same manner as in Embodiment 1, image processing unit 9 calculates a received signal on an intersecting point of the ultrasound beam of aperture 16 in the normal-line direction and in the direction of the inclined ultrasound beam of aperture 14 using a compound scan image forming method, and a tomographic image parallel to the Y-axis direction is generated. Here, according to Embodiment 2, apertures 16 and 14 perform scans in the Y-axis direction at every movement thereof in the X-axis direction. Therefore, a plurality of two-dimensional tomographic images are generated in the normal-line direction of the probe surface and in the Y-axis direction along the X-axis direction.

Here, for example, if an examiner operates an operation panel (not shown) installed in the ultrasonic diagnostic apparatus according to Embodiment 2 to instruct display of a three-dimensional image, image processing unit 9 first generates a three-dimensional image from a plurality of tomographic images. Next, image processing unit 9 performs known image processings, such as a volume rendering, to convert the three-dimensional image into a two-dimensional image (three-dimensional ultrasound image) for display, and displays it on monitor 10.

As described above, in the ultrasonic diagnostic apparatus according to Embodiment 2, an ultrasound beam of aperture 16 in the normal-line direction of the probe surface and an ultrasound beam of aperture 14 in a direction oblique with respect to the ultrasound beam of aperture 16 are caused to scan an identical cross section and collect a tomographic image. Next, according to Embodiment 2, image processing unit 9 generates one tomographic image using a compound scan image forming method in which tomographic information on an intersecting point of the ultrasound beams is generated from the tomographic information collected by ultrasound beams in the different directions. Here, if an examiner operates a button of an operation panel (not shown) to instruct display of the tomographic image, i.e. the two-dimensional image, image processing unit 9 sequentially outputs and displays the tomographic image generated with the compound scan onto the display screen of the monitor 10.

Meanwhile, in a case where the examiner operates a button of the operation panel (not shown) to instruct display of a three-dimensional image, image processing unit 9 reconstructs a three-dimensional image from the plurality of tomographic images generated with the compound scan. Next, image processing unit 9 performs the known volume rendering processing on the reconstructed three-dimensional image to generate a three-dimensional image for display (three-dimensional plane image) and outputs the thus-generated three-dimensional plane image, which is presented on the display screen.

In this case, an ultrasound beam scan in the normal-line direction of the probe surface is performed by Fresnel-ring aperture 16 including one portion of all transducer elements 4, an ultrasound beam scan in a different direction than the normal-line direction of the probe surface is performed by strip-shaped aperture 14, and an ultrasound tomographic image is calculated from ultrasound data obtained by the respective apertures. Accordingly, received wave phasing unit 7 can be constructed without increasing the apparatus scale, i.e. with a fewer number of channels than the number of transducer elements 4, while an ultrasound tomographic image of high resolution can be obtained using the two-dimensional ultrasound probe. Therefore, the image quality of the ultrasonic diagnostic apparatus can be improved, while received wave phasing unit 7 is constructed without increasing the apparatus scale, i.e. with a fewer number of channels than the number of transducers 4.

Meanwhile, although aperture 16 and aperture 14 of the ultrasonic diagnostic apparatus according Embodiment 2 perform scans in the Y-axis direction, the scan direction is not limited thereto, and, of course, it may be in any direction in the probe surface. In this case, however, it is necessary to construct strip-shaped aperture 14 with a small number of element selecting switches and channels. Therefore, the bundling direction of transducer elements bundled into strip shapes have to be set in correspondence with the scan direction of the ultrasound beam. For example, aperture 14 can perform a scan in a 45-degree direction between the X- and Y-axes by bundling a plurality of strips perpendicular to the scan direction.

Further, in the ultrasonic diagnostic apparatus according to Embodiment 2, scans of aperture 16 and aperture 14 are sequentially performed, and a three-dimensional image of high resolution is generated from the thus-collected tomographic images. Meanwhile, for example, it is also possible for the main body or the probe unit of the ultrasonic diagnostic apparatus according to Embodiment 2 to be given a mode of displaying a tomographic image or of generating a three-dimensional image obtained by ultrasound scans of either of aperture 16 or aperture 14 and a mode of generating a tomographic image combining the tomographic images obtained by aperture 16 and aperture 14 with a compound scan or generating and displaying a three-dimensional image from thus-generated tomographic images. With this construction, it is possible to detect an ROI on the basis of the tomographic image or the three-dimensional image obtained in the ultrasound scan mode of either of aperture 16 or aperture 14, and the mode is shifted to the other mode for generating and displaying a combined tomographic image or a three-dimensional image when a tomographic image of high image quality of the ROI is needed. Thus, the ROI can be immediately detected and observed using an image of high image quality (definite diagnosis). As a result, the diagnostic efficiency can be improved.

Further, in the ultrasonic diagnostic apparatus according to Embodiment 2, the ultrasound beam may be inclined in the Y-axis direction, as shown in FIG. 5(c). Besides, it can also be inclined in the X-axis direction by setting aperture 14' formed by the transducers selected in strip-shapes in the Y-axis direction from among transducer elements 4.

When a compound scan is performed using the ultrasound beam inclined in the X-axis direction or in another direction as well, the area surrounded by the transducer elements 4 is controlled so that a tomographic image is generated from tomographic information on a position where the ultrasound beams intersect on the basis of an ultrasound tomographic image obtained by scans of the ultrasound beams in the different beam directions in a similar manner to that described above.

Accordingly, scans and image generation can be performed in any direction in the probe surface, whereby ultrasound diagnosis can be conducted on a wider area by waving the ultrasound beam also in the X-axis direction. Further, focusing can be done in the row direction of one transducer array of aperture 14 as in the above-described Embodiment 1.

EMBODIMENT 3

Figure 6:
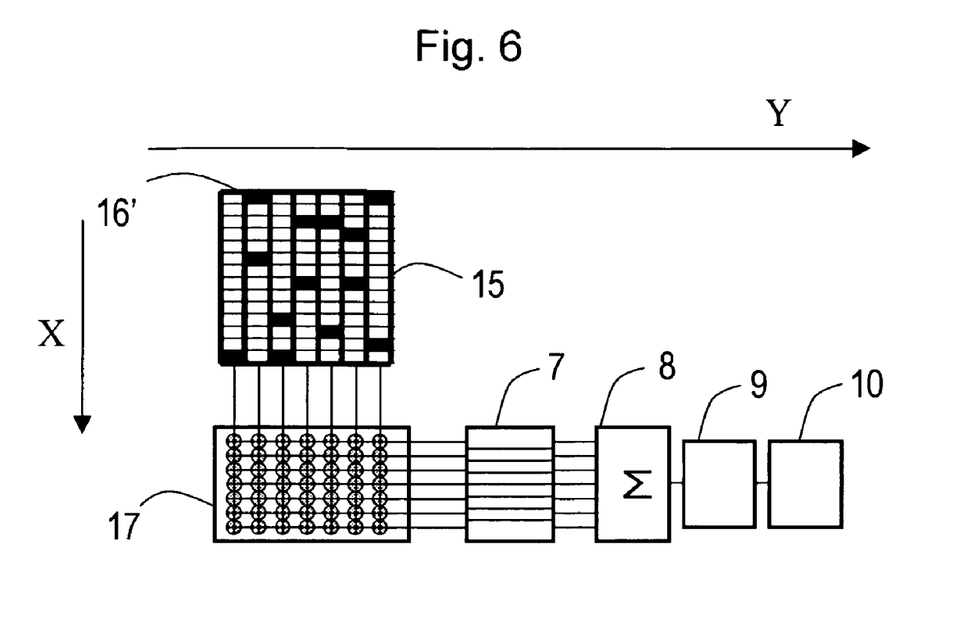
FIG. 6 is a diagram illustrating the structure of an ultrasonic diagnostic apparatus according to Embodiment 3 of the present invention.
Figure 7:
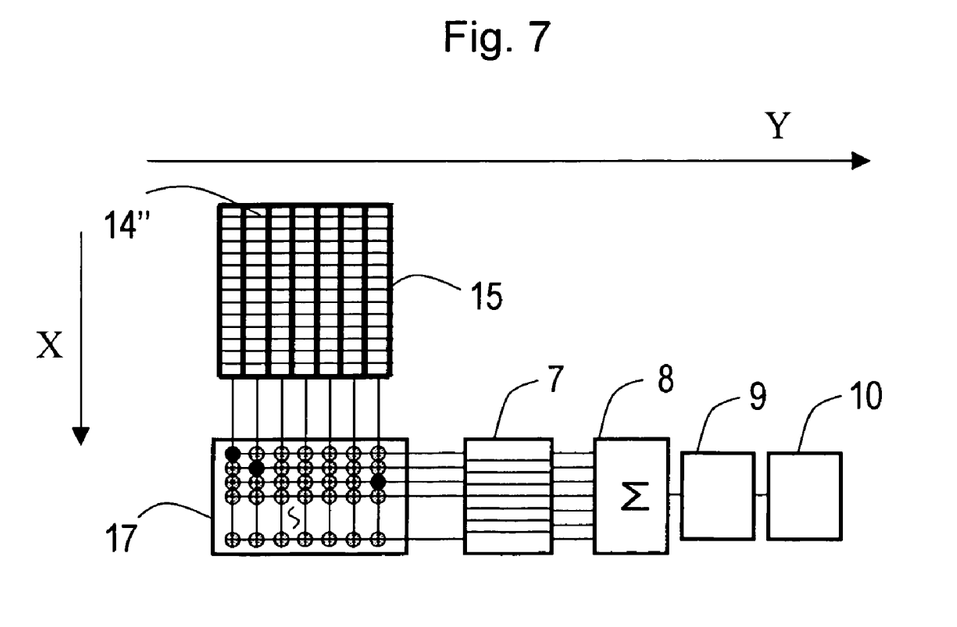
FIG. 7 is a diagram illustrating the structure of an ultrasonic diagnostic apparatus according to Embodiment 3 of the present invention.

FIG. 6 and FIG. 7 are diagrams illustrating the structure of an ultrasonic diagnostic apparatus according to Embodiment 3 of the present invention. Specifically, FIG. 6 is a diagram illustrating collection of tomographic image data using the aperture of a sparse array 16', and FIG. 7 is a diagram illustrating collection of tomographic image data using the aperture of transducer elements bundled into strip shapes. As an example, according to Embodiment 3, a two-dimensional array probe including 64×64=4096 transducer elements 4 is used. However, the number of transducer elements is not limited to 4096. Further, although a conventional sparse array does not need the array switch 17 in which a plurality of element selecting switches are arranged, transducer element 4 is connected to received wave phasing unit 7 through array switch 17 according to Embodiment 3. With this structure, ultrasound transmission and reception of both sparse array 16' and of transducer elements 4 bundled into strip shapes are performed in an identical two-dimensional array probe by flipping the element selecting switch. That is, while the probe is applied to the object (not shown), ultrasound measurement can be switched between the sparse array and of the trip-shaped aperture 14'.

In the ultrasonic diagnostic apparatus according to Embodiment 3, as shown in FIG. 6, 128 transducer elements among the 64×64=4096 transducer elements 4 form a so-called sparse array used in ultrasound transmission and reception. However, in the ultrasound measurement of sparse array 16', the transducer elements used in transmission and reception are fixed. Accordingly, control means (not shown) operates to switch on the predetermined element selecting switch among those forming array switch 17 to fix transducer elements used in wave transmission and those used in wave reception. This structure enables ultrasound measurement using the sparse array. In the scan of the sparse array, predetermined phasing data is supplied to the respective transducers and the inside of a circular cone having a top forming one point of the array surface is three-dimensionally scanned.

On the other hand, in the ultrasound measurement of transducer elements 4 bundled into strips, 64×64 transducer elements 4 are bundled into a plurality of rows, e.g. 64 rows, of strips. Thus, the strip-shaped aperture 14" including all of the 64×64=4096 transducer elements 4 is formed. At this time, by adjusting the delay data or phasing data supplied to a transmission signal supplied to transducer elements forming aperture 14" and the received signal output from the transducers, a central position of ultrasound beams of aperture 14" is set on a position shifted from the center of aperture 14" (different position than the scan center of sparse array 16'). Next, a tomographic image of the object (not shown) is collected by a sector scan with respect to the position shifted from the central position of the aperture 14". That is, the tomographic image of the object is collected by the sector scan, wherein the intersecting positions of the ultrasound beams formed by ultrasound transmission and reception of aperture 14" and the probe surface is shifted from the central position of aperture 14" in the Y-axis direction to a predetermined distance. Meanwhile, the ultrasound beam is formed by applying a delay to each of the received signals output from the transducer elements at received wave phasing unit 7 and by summing up the received signals at signal processing unit 8 after applying the delay.

Further, the channel number of received wave phasing unit 7 for the sparse array is about four times that of the traditional apparatus. Therefore, in performing aperture 14" according to Embodiment 3, changing the connection of the array switch 17 and dividing the strips in the longitudinal direction (X-axis direction) to be connected with received wave phasing unit 7 are performed, whereby the resolution and the S/N ratio of the collected tomographic image are further improved over those obtained with the sparse array.

Next, image processing unit 9 performs a calculation based on information on the intersecting positions of the ultrasound beams of tomographic images collected by aperture 16' and by aperture 14", and a tomographic image and/or a three-dimensional image is generated from the calculated image data on the intersecting positions. Here, when display of the tomographic image is selected from an operation board (not shown), image processing unit 9 converts the generated tomographic image into data for display and outputs the data to monitor 10 to present it on the display screen. Meanwhile, when display of the three-dimensional image is selected, image processing unit 9 generates a two-dimensional image (three-dimensional ultrasound image) for display, which is generated from the three-dimensional image, outputs it to monitor 10 after converting this three-dimensional ultrasound image into data compatible with the input format of monitor 10, and displays the three-dimensional ultrasound image on the screen of monitor 10.

As described above, in the ultrasonic diagnostic apparatus according to Embodiment 3, sparse array aperture 16' and strip-shaped aperture 14", which are formed over the probe surface of the two-dimensional array probe, perform a sector scan of an ultrasound beam on a desired cross section, while the central position of the ultrasound beams of the strip-shaped aperture 14" is set to a position shifted from the central position of aperture 16' to a predetermined degree. In this manner, received wave phasing unit 7 is constructed without increasing the apparatus scale, i.e. with a fewer number of channels than transducer elements 4, and an ultrasound image on a desired cross section can be collected in which the ultrasound beams of aperture 16' and of aperture 14" intersect, whereby, with a compound scan, a tomographic image of more improved image quality than each tomographic image can be generated. Accordingly, even when a three-dimensional image is generated by collecting a plurality of tomographic images with a compound scan, the image quality of the three-dimensional image can be improved, and that of a three-dimensional ultrasound image forming an ultrasound image for display generated from the three-dimensional image can also be improved.

In the ultrasonic diagnostic apparatus according to Embodiments 1 and 2, the form of aperture 16' is a Fresnel ring concentrically bundling the elements. However, it is not limited thereto, and, of course, it may be formed in an arbitrary shape such as an ellipse, a rectangle, and the like, by shifting the element selecting switch. In this case, aperture 16' transmits and receives an ultrasound beam that is focused in accordance with the arbitrary shape. However, it is needless to say that when aperture 16' is formed in the Fresnel-ring shape, the phasing circuit can be constructed with the least number of channels, and an ultrasound image of good S/N ratio can be obtained.

Although Embodiments 1 to 3 have been described for the case of generating a three-dimensional ultrasound image, they are not limited thereto and may have another structure. For example, when a three-dimensional image is reconstructed from tomographic images collected by Fresnel-ring aperture 16, the thus-obtained three-dimensional image is presented on monitor 10, and a tomographic image on an assigned cross section is obtained on the basis of the tomographic image displayed on the monitor 10. It is needless to say that a tomographic image generated from tomographic images obtained with aperture 16 and aperture 14 may be displayed. With this structure, it is possible to perform measurement of the tomographic images of aperture 16 and aperture 14, which takes a relatively long time, only on a collected tomographic image generally required in a definite diagnosis, whereby it is possible to reduce the time taken for collecting the tomographic image required in definite diagnosis. As a result, it is possible to reduce the burden on the object and to improve the diagnostic efficiency.

Although Embodiments 1 to 3 only employ a compound scan using two ultrasound images, the compound scan combining three or more ultrasound images may be performed. Further, although a three-dimensional display is produced by performing volume rendering processing on the scanned volume data in the above-described embodiments, the invention is not limited thereto. For example, it may be done in a manner such that a point of view is determined and a two-dimensional image taken from the point of view is displayed by determining transmittance in each voxel as if a light is transmitted through the two-dimensional image in accordance with the sound intensity along the line of vision.

Further, a plurality of collected tomographic images may be sequentially presented in accordance with the operation of an image switching button provided on the control board. That is, although a three-dimensional plane image is generated with the volume rendering processing according to Embodiments 2 and 3, the manner of generating the three-dimensional plane image to be displayed from the three-dimensional image is not limited to the use of volume rendering processing, and it may be produced in another manner. Further, the display format is not limited to that of a two-dimensional image and may be a known display format of a three-dimensional image.

Further, although the scan method is changed in units of a frame, it may be changed at every raster to produce compound data at each raster and perform a scan.

The invention has been described in detail in accordance with various embodiments thereof. However, the present invention is not limited to those embodiments and various changes may be made within the scope of the invention.

The invention claimed is:

1. An ultrasonic diagnostic apparatus comprising:
   an ultrasound probe in which a plurality of transducer elements for transmitting and receiving an ultrasonic wave to/from an object to be examined two-dimensionally arranged;
   transducer element selecting means for selecting a transducer element to be used in ultrasound transmission and reception;
   a signal processing unit for applying a delay time to a received wave signal received by the selected transducer element and performing signal processing;
   an image processing unit for generating an image on the basis of a signal output by the signal processing unit; and
   an image display unit for displaying the generated image, wherein
   the image processing unit includes storing means for storing a first ultrasound image obtained by a scan performed with a first transducer arrangement selected by the transducer element selecting means and a second ultrasound image obtained by a scan performed with a second transducer arrangement selected by the transducer element selecting means so as to irradiate an ultrasound beam in a different direction than a beam direction of the first transducer arrangement, and image calculating means for combining the first ultrasound image and the second ultrasound image.

2. An ultrasonic diagnostic apparatus according to claim 1, wherein a beam formed by the second transducer arrangement intersects with that formed by the first transducer arrangement.

3. An ultrasonic diagnostic apparatus according to claim 1, wherein the image calculating means generates a combined image from tomographic information on a position where the ultrasound beams of the first ultrasound image and of the second ultrasound image intersect with each other.

4. An ultrasonic diagnostic apparatus according to claim 1, wherein the first ultrasound image is obtained by moving an aperture formed in the first transducer arrangement on a surface of the ultrasound probe and the second ultrasound image is obtained by moving an aperture formed in the second transducer arrangement on the surface of the ultrasound probe.

5. An ultrasonic diagnostic apparatus according to claim 1, wherein the second ultrasound image is collected on the same portion as the first ultrasound image.

6. An ultrasonic diagnostic apparatus according to claim 1, wherein the image processing unit reconstructs a three-dimensional image from a plurality of ultrasound images.

7. An ultrasonic diagnostic apparatus according to claim 4, wherein the first ultrasound image is obtained by two-dimensionally moving the aperture of the first transducer arrangement on the surface of the ultrasound probe, and the second ultrasound image is obtained by moving the aperture of the second transducer arrangement in correspondence with a moving path of the first received signal.

8. An ultrasound diagnostic apparatus according to claim 1, wherein the first transducer arrangement or the second transducer arrangement is a separate array which forms a central position of ultrasound beams at a different position than that of ultrasound beams of the other transducer array.

9. An ultrasonic diagnostic apparatus according to claim 1, wherein the direction of the beam of the first transducer arrangement coincides with the direction of a normal line with respect to a body surface of the object.

10. An ultrasonic diagnostic apparatus according to claim 9, wherein the first transducer arrangement is a ring-shaped aperture and the second transducer arrangement is a strip-shaped aperture.

11. An ultrasonic diagnostic apparatus according to claim 10, wherein the transducer elements forming the ring-shaped aperture are selected so that the distances from the respective transducer elements to a focal point are identical.

12. An ultrasonic diagnostic apparatus according to claim 10, wherein in the second transducer arrangement, an oblique angle of ultrasound beam is arbitrarily set by adjusting phasing data for each transducer element row.

13. An ultrasonic diagnostic apparatus according to claim 1, wherein in the first transducer arrangement or the second transducer arrangement, an oblique angle of ultrasound beam is arbitrarily set by adjusting phasing data for each transducer element row.

14. An ultrasonic diagnostic apparatus according to claim 1, wherein an arrangement surface of the transducer elements forms a convex shape in a direction of ultrasound transmission.

15. An ultrasonic diagnostic apparatus according to claim 1, wherein the first transducer arrangement or the second transducer arrangement is divided into a plurality of transducer groups, and each transducer group is provided with a phasing circuit.

16. An ultrasonic diagnostic apparatus of claim 1, wherein the two-dimensional transducer elements are arranged to form a two-dimensional transducer element array.

17. An ultrasonic diagnostic apparatus of claim 1, wherein at least one of the first scan and the second scan includes an oblique scan, in which the direction of ultrasound beam forms an angle between 0° and 90° with respect to the surface normal of the transducer element array in the plane defined by the direction of ultrasound beam and the surface normal.

18. An ultrasound imaging method using an ultrasound probe including a two-dimensional array of transducer elements for transmitting and receiving an ultrasonic wave, comprising the steps of:
   selecting a transducer element forming a first transducer arrangement and obtaining a first ultrasound image with an ultrasound scan;
   selecting a transducer element forming a second transducer arrangement generating an ultrasound beam in a direction intersecting with the direction of the beam of the first transducer arrangement and obtaining a second ultrasound image with an ultrasound scan;
   storing the first ultrasound image and the second ultrasound image; combining the first ultrasound image and the second ultrasound image; and
   displaying the combined image.

19. An ultrasound imaging method according to claim 18, wherein at least one of the first scan and the second scan includes an oblique scan, in which the direction of ultrasound beam forms an angle between 0° and 90° with respect to the surface normal of the transducer element array in the plane defined by the direction of ultrasound beam and the surface normal.

* * * * *